United States Patent [19]

Jackson

[11] Patent Number: 4,596,244
[45] Date of Patent: Jun. 24, 1986

[54] PERINEAL DRAPE

[75] Inventor: Elizabeth M. Jackson, Norcross, Ga.

[73] Assignee: Kimberly-Clark Corporation, Neenah, Wis.

[21] Appl. No.: 581,457

[22] Filed: Feb. 17, 1984

[51] Int. Cl.⁴ ............................................. A61F 13/00
[52] U.S. Cl. ............................. 128/132 D; 2/DIG. 7; 604/389; 604/358
[58] Field of Search ....................... 128/132 D, 132 R; 604/358, 386, 389, 385, 387; D24/50; 2/DIG. 7

[56] References Cited

U.S. PATENT DOCUMENTS

| | | | |
|---|---|---|---|
| 3,625,205 | 12/1971 | Madden et al. | 128/132 D |
| 3,731,688 | 5/1973 | Litt et al. | 604/385 |
| 3,889,667 | 6/1975 | Collins | 128/132 D |
| 3,938,523 | 2/1976 | Gilliland et al. | 604/385 R |
| 3,978,860 | 9/1976 | Stima | 604/385 R |
| 4,108,179 | 8/1978 | Schaar | 604/385 R |

Primary Examiner—Robert P. Swiatek
Assistant Examiner—John G. Weiss
Attorney, Agent, or Firm—William D. Herrick

[57] ABSTRACT

A folded hospital drape for placing on a patient by operating room personnel has a generally rectangular center section and side sections C-folded inwardly over the center section. The drape is folded and secured to form a narrow drape area for fitting between the legs in the crotch of a patient. Adhesive strips on the flaps and an adhesive strip across the end of the drape are provided for securing the drape to the thighs and abdomen of the patient when the center section and the side sections are spread to form a wide drape area at the end of the drape. The opposite end of the drape is tucked under the patient's buttocks. A cuff section at the top end of the drape is provided so that the hands of the person applying the drape to the patient may be inserted in the cuff to spread the side sections of the drape outwardly from the center section.

6 Claims, 10 Drawing Figures

PERINEAL DRAPE

TECHNICAL FIELD

This invention relates to a folded hospital drape and, more particularly, to a drape for covering the perineal area during surgical operations.

BACKGROUND ART

In a surgical operation such as a coronary bypass where the saphenous vein is removed from the leg or thigh of the patient undergoing the bypass operation, there is a need for a hospital drape that can be attached to a patient's abdomen and which will wall off the entire perineum. There is a further need for such a hospital drape that can be attached without using stitches or clips to the skin. There is also a need for a drape which, while small in size, has a shape that covers the entire perineum without use of excessive material. For other types of surgical operations in this body area, there is also a need for a hospital drape that can be used to cover the entire perineum and can be secured easily in position.

Heretofore woven fabric towels customarily have been used for this purpose. These towels are folded lengthwise to the required width, placed on the perineum, tucked under the buttocks and secured to the lower abdomen by towel clips or stitches.

Certain problems are raised when towels are used for draping the patient during such surgical operations. For example, fabric towels are absorbent and porous and may allow fluid and bacteria to penetrate from the perineum and contaminate the operative site or sites. When towels are clipped or stitched to the lower abdomen, the sides of the towels are left open, which allows fluids and bacteria to travel to and from the perineal area. Also, the stitches and towel clips are invasive and traumatic and may produce sites for infection where the skin is penetrated by the stitching needles. In addition, it is very difficult for the sterile operating room personnel who are draping the patient with such towels to avoid touching the patient's skin during the draping procedure. To avoid contamination, they must not touch the patient's body, particularly in the perineal area.

DISCLOSURE OF INVENTION

The principal object of this invention is to provide a perineal drape that protects the patient by walling off the "dirty" perineum from an open incision, for example, in the chest or leg during a coronary bypass, or in the abdomen during an appendectomy. In accomplishing this objective, a drape is provided that has a shape to cover entirely the perineum and has adhesive on the surface of the drape to attach the drape without requiring stitches or clips in a manner that provides an effective wall and prevents bacteria transfer from the perineum, that has fluid repellency to contain fluid and prevent it from penetrating or passing the sides of the drape, and that has cuffs to cover the hands of the person applying the drape to prevent contact with the patient's body and contamination of the person applying the drape.

BRIEF DESCRIPTION OF THE DRAWINGS

Further objects will appear from the following description taken in connection with the accompanying drawings in which.

BEST MODE FOR CARRYING OUT THE INVENTION

Figure 1:
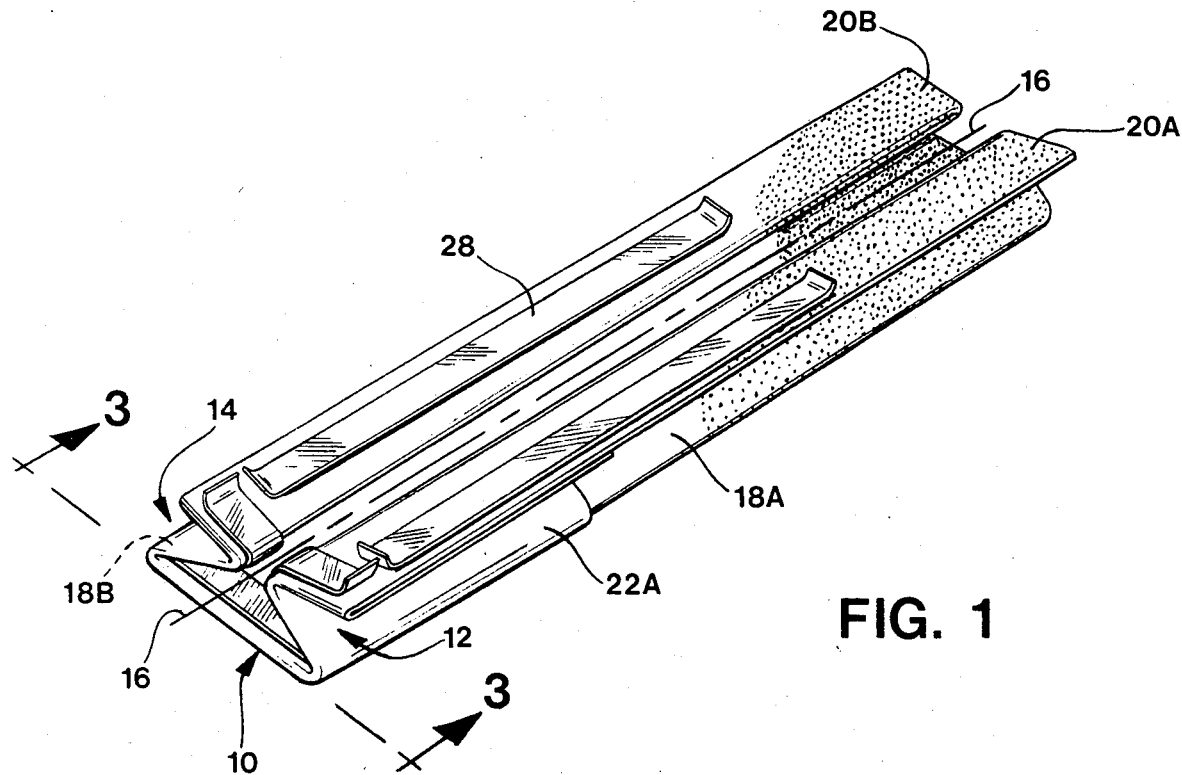
FIG. 1 is a perspective view of a folded perineal drape constructed according to this invention.

Turning to the drawings, a drape according to this invention is shown in FIG. 1 in a condition ready to be placed on a patient by operating room personnel. The drape in this condition has folds somewhat similar to a wing-folded rectangular diaper with a generally rectangular center section 10 and with side sections 12, 14 C-folded inwardly over the center section 10 to provide on each side of the longitudinal center line 16 an inwardly extending portion 18A, 18B and an outwardly extending flap 20A, 20B. In keeping with this invention, the drape is provided with a cuff section 22A, preferably at one end, and also is provided with pressure sensitive adhesive strips 24A, 24B extending longitudinally on the flaps of the side sections and in a single strip 26 extending transversely across one end of the drape, the end strip 26 extending substantially continuously adjacent the edge of the drape on both the center and the side sections (as shown more clearly in the unfolded drape shown in FIG. 8). Such adhesive strips 24A, 24B, 26 are covered with strips of release paper 28 for packaging, which is peeled from the adhesive when the drape is placed on the patient.

Figure 9:
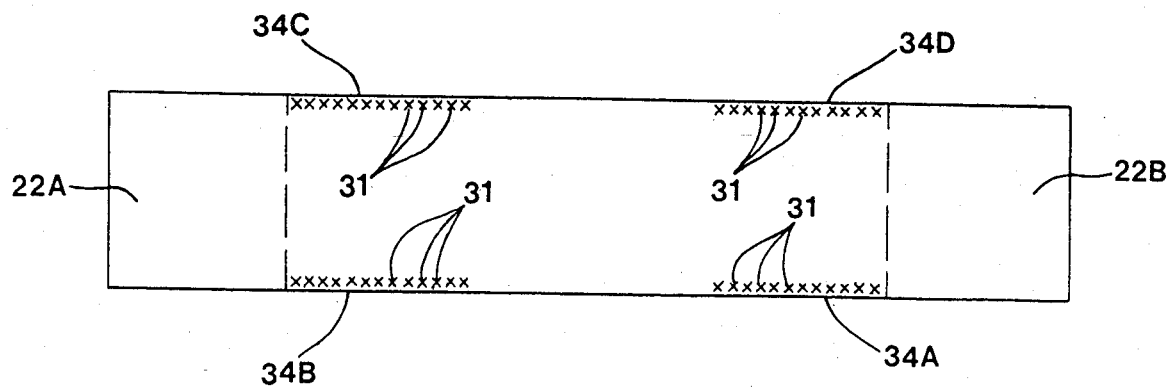
FIG. 9 is a view similar to FIG. 6 of the starting sheet of material before folding into an alternative embodiment of the drape of this invention.
Figure 10:
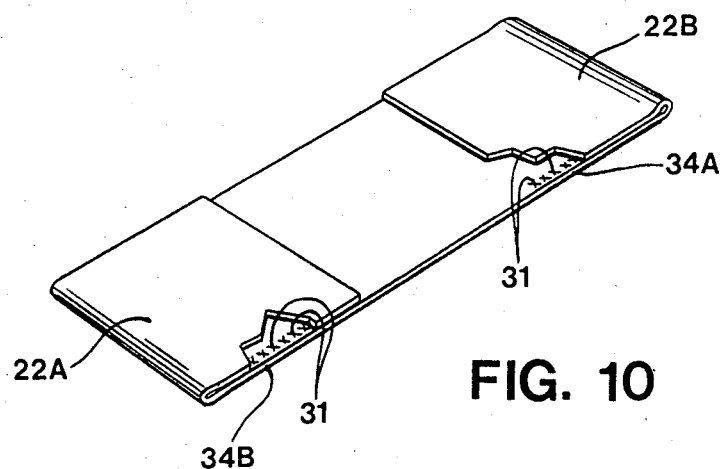
FIG. 10 is a perspective view of the sheet of material shown in FIG. 9, partially folded to provide the cuff sections at both ends.

To hold the drape in folded condition, the inner portions 18A, 18B of the side sections 12, 14 are secured to locations 30, 32 intermediate the ends of the center section 10 of the drape, it being most preferred to secure the inner portions 18A, 18B by adhesive at such locations, although other securing means could be used if desired. With the inner portions 18A, 18B secured to the center section 10 at intermediate locations 30, 32, the drape is held at such locations to form a narrow drape area for fitting between the legs in the crotch of a patient. The adhesive strips 24A, 24B on the flaps 20A, 20B and the adhesive strip 26 across the end of the drape are provided for securing the drape to the thighs and abdomen of the patient when the center section 10 and the side sections 12, 14 are spread to form a wide drape area at the end of the drape. The opposite end of the drape is tucked under the patient's buttocks. With the cuff section 22A at the top end of the drape, the hands of the person applying the drape to the patient may be inserted in the cuff to spread the side sections 12, 14 of the drape outwardly from the center section 10 at the end of the drape while the narrow area intermediate the ends is held in the folded condition by the securement means at the locations 30, 32. In an alternative embodiment shown in FIGS. 9 and 10, a second cuff section 22B at the lower end of the drape may also be provided to allow the hands of the person applying the drape to be inserted in the second cuff to avoid touching the skin of the patient and to facilitate its placement. However, the second cuff at the lower end of the drape may be omitted, as shown in FIG. 1, and the end of the drape tucked in the draped position, the provision of the second cuff being optional.

To make a drape according to this invention, a rectangular sheet of drape fabric is provided, preferably a nonwoven fabric of about 1.4 ounce basis weight which has a laminar construction, as disclosed in U.S. Pat. No. 4,041,203, and includes an integrated mat of polymeric microfibers united to and sandwiched between outer webs of continuous polymeric filaments. Preferably the drape fabric is treated in a conventional manner to be fluid repellent.

Figure 6:
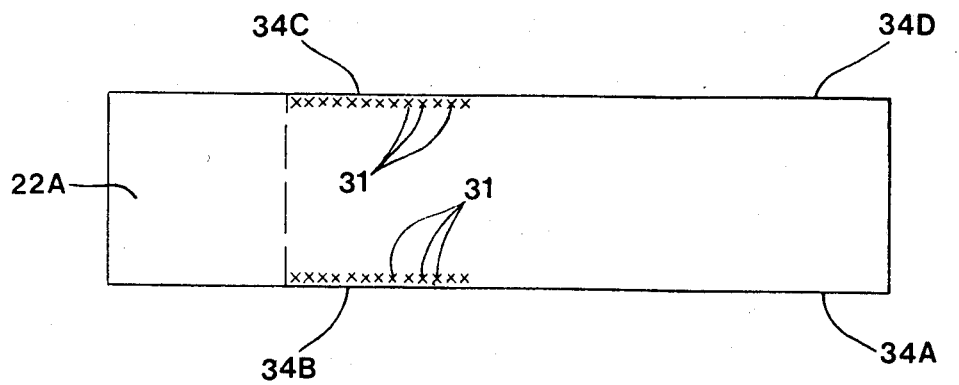
FIG. 6 is a plan view of the starting sheet of material before folding into the drape of FIG. 1.

While the drape may be made in larger or smaller sizes, in an exemplary embodiment the starting sheet size is a rectangle, as pictured in FIG. 6, 32.5 inches in length and 10.5 inches in width. In this embodiment, a cuff section 22, approximately 7.5 inches in length, is folded in from one end, as shown in FIG. 7, and fastened by adhesive or other seaming methods (indicated diagrammatically at 31) to the side edges 34A, 34B of the side sections of the drape fabric.

Figure 7:
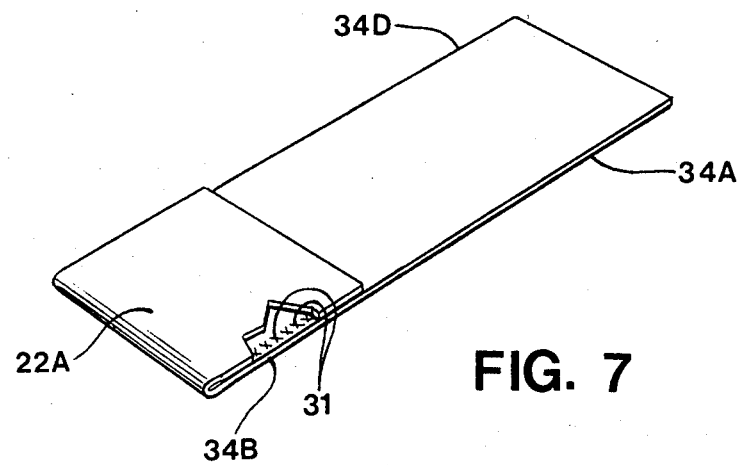
FIG. 7 is a perspective view of the sheet of material partially folded to provide the cuff section.
Figure 8:
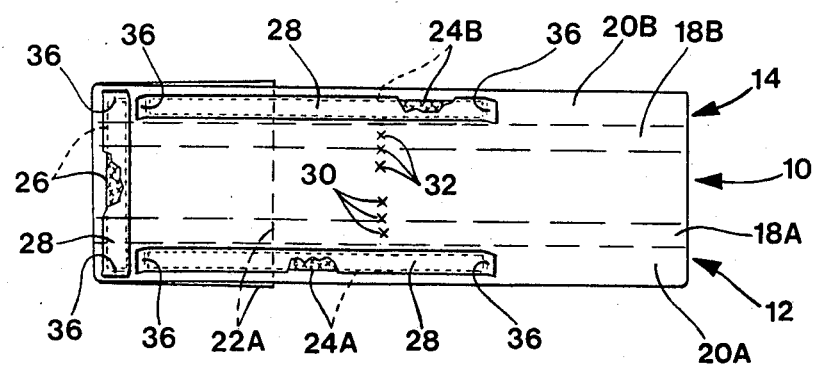
FIG. 8 is a plan view of the partially folded sheet of FIG. 7, turned over to show the adhesive strips applied to the sheet, before folding into the drape as shown in FIG. 1.

The partially folded drape, as shown in FIG. 7, is then turned over to the position shown in FIG. 8, thus providing the cuff section 22A beneath the center section 10 and side sections 12, 14 (when spread outwardly as shown in FIG. 8). Pressure sensitive adhesive is applied in strips 24A, 24B, 26 along the margins of the drape fabric. These strips of adhesive may be applied using strips of release paper, preferably leaving tabs 36 to facilitate removing the strips of release paper when the drape is placed on the patient. Tacky adhesive is also placed at locations 30, 32 intermediate the longitudinal ends of the center section 10.

To provide the folded drape shown in FIG. 1 from the partially folded drape of FIG. 8, the side sections 12, 14 are folded over the center section 10; the adhesive at the locations 30, 32 acts to secure both inner portions 18A, 18B to the center section 10 to hold the drape folded at such locations for fitting to the patient. The resulting folded drape structure is relatively long and narrow, the ratio of length to width being preferably about 8:1, to provide sufficient drape fabric to completely cover the perineum while being narrow to avoid excessive bunching of material in the crotch. With the drape being made of flexible drape fabric, the end portion with the cuff may be laid flat and conforms to the patient's body such that it may be adhered in place with the adhesive and wall off the perineum from sites of incisions in the patient's body. The other end portion of the drape provides sufficient fabric to be tucked under the buttocks.

Figure 2:
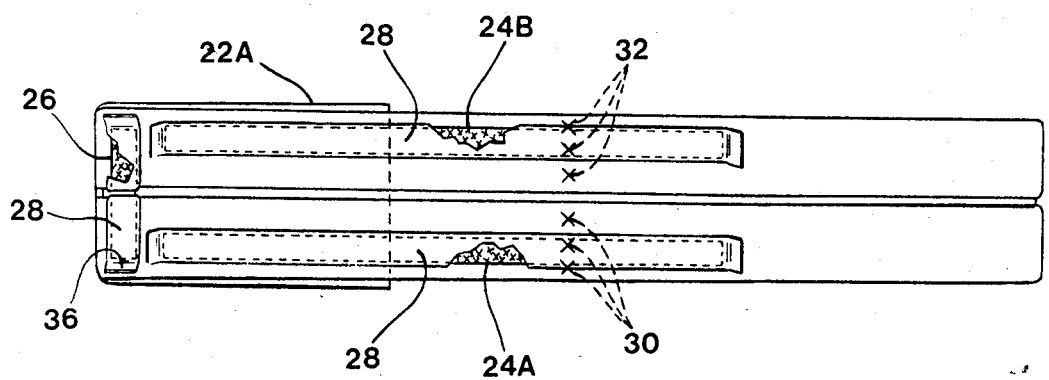
FIG. 2 is a plan view of the folded drape shown in FIG. 1.
Figure 3:
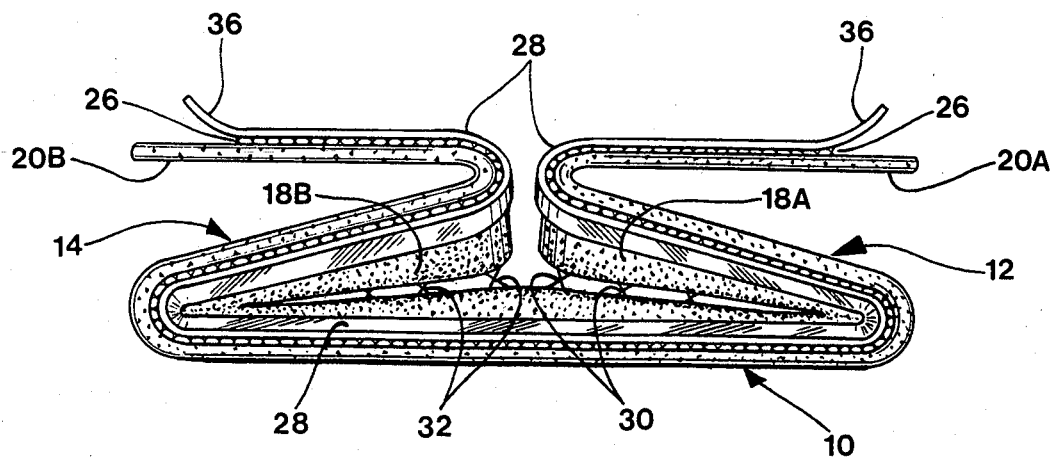
FIG. 3 is an end view of the drape shown in FIG. 1.
Figure 4:
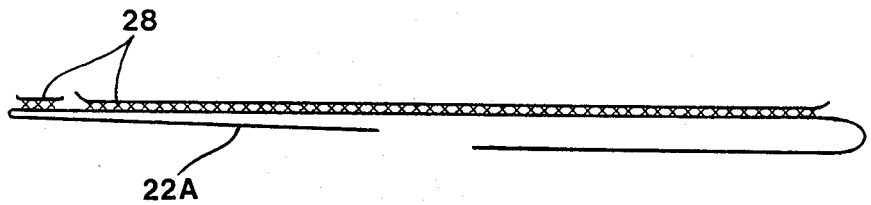
FIG. 4 is a diagrammatic view of the drape shown in FIGS. 1 and 2, with one further lengthwise fold for packaging.
Figure 5:
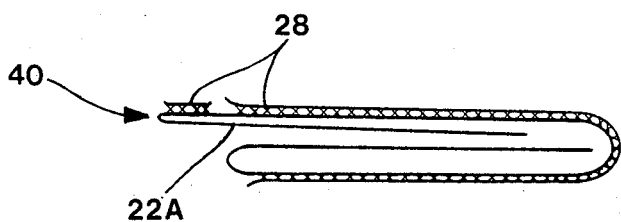
FIG. 5 is a diagrammatic view of the drape with a second lengthwise fold, ready for packaging.

For packaging, as shown in FIGS. 1 and 2, the drape is folded with a fold lengthwise as shown in FIG. 4 and with a second fold lengthwise as shown in FIG. 5 to provide the drape ready for packaging. After removal from the package, the drape is presented with the top end 40 (FIG. 5) having a cuff so that the drape may be shaken out and easily handled by the operating room person to place it on the patient.

I claim:
1. A surgical drape of fluid repellent material and adapted to wall of the perineum from incision sites comprising:
 (1) a generally rectangular center section having a longitudinal center line,
 (2) side sections extending from said center section and C-folded over said center section to provide on each side of said center line an inwardly extending portion and an outwardly extending flap,
 (3) a cuff section having a portion located at one end of said center section,
 (4) means for securing both inner portions of said side sections to locations intermediate the longitudinal ends of said center section to hold the drape folded at such locations to form a narrow drape area for fitting between the legs in the crotch of a patient, and
 (5) adhesive means extending longitudinally on the outer flaps of said side sections and transversely on said one end on the center section and on both the inner portions and outer flaps of said side sections for securing said sections when spread to form a wide drape area to the thighs and the abdomen of a patient with the other end of said center and side sections under the buttocks of the patient.

2. A surgical drape according to claim 1 further including means securing said cuff section to side edges of said sections.

3. A surgical drape according to claim 1 in which said cuff section extends adjacent said center section and both side sections.

4. A surgical drape according to claim 1 further including a second cuff section at the end of said center and side sections remote from said first cuff section, said second cuff section having a portion located under said center section and portions extending adjacent both side sections.

5. A surgical drape according to claim 1 in which said first and second cuff sections are secured to side edges of said side sections.

6. A surgical drape of fluid repellent material and adapted to wall off the perineum from incision sites comprising:
 (1) a generally rectangular center section having a longitudinal center line,
 (2) side sections extending from said center section and C-folded over said center section to provide on each side of said center line an inwardly extending portion and an outwardly extending flap,
 (3) a cuff section having a portion located at one end of said center section,
 (4) means for securing both inner portions of said side sections to locations intermediate the longitudinal ends of said center section to hold the drape folded at such locations to form a narrow drape area for fitting between the legs in the crotch of a patient, and
 (5) pressure sensitive adhesive covered by a release strip on the outer flaps of said side sections and on said one end on the center section and on both the inner portions and outer flaps of said side sections for securing said sections when spread to form a wide drape area to the thighs and the abdomen of a patient with the other end of said center and side sections under the buttocks of the patient.

* * * * *